United States Patent
Hirokami

(10) Patent No.: US 9,238,663 B2
(45) Date of Patent: Jan. 19, 2016

(54) ORGANOSILICON COMPOUNDS, MAKING METHODS, AND ADHESION IMPROVER

(71) Applicant: Shin-Etsu Chemical Co., Ltd., Chiyoda-ku, Tokyo (JP)

(72) Inventor: Munenao Hirokami, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/709,727

(22) Filed: May 12, 2015

(65) Prior Publication Data

US 2015/0239913 A1   Aug. 27, 2015

Related U.S. Application Data

(62) Division of application No. 14/258,105, filed on Apr. 22, 2014.

(30) Foreign Application Priority Data

Jun. 12, 2013  (JP) .................................. 2013-123638

(51) Int. Cl.
| | |
|---|---|
| *C07F 7/10* | (2006.01) |
| *C07F 7/18* | (2006.01) |
| *C08K 5/44* | (2006.01) |
| *C07F 7/08* | (2006.01) |
| *C08K 5/41* | (2006.01) |
| *C08K 9/06* | (2006.01) |

(52) U.S. Cl.
CPC ................. *C07F 7/1804* (2013.01); *C07F 7/08* (2013.01); *C07F 7/10* (2013.01); *C07F 7/1836* (2013.01); *C08K 5/41* (2013.01); *C08K 5/44* (2013.01); *C08K 9/06* (2013.01)

(58) Field of Classification Search
CPC ........... C07F 7/08; C07F 7/1804; C08K 9/06; C08K 5/41; C08K 5/44
USPC ....................... 556/12, 431; 524/282; 106/481
See application file for complete search history.

(56) References Cited

U.S. PATENT DOCUMENTS 7,968,204 B2   6/2011   Koh et al.

FOREIGN PATENT DOCUMENTS

| EP | 2 147 685 A1 | 1/2010 |
|---|---|---|
| EP | 2 524 923 A1 | 11/2012 |
| JP | 4692885 B2 | 6/2011 |
| WO | WO 03/014248 A2 | 2/2003 |
| WO | WO 2004/074344 A1 | 9/2004 |

OTHER PUBLICATIONS

Database Chemabs [Online], Chemical Abstracts Service, Columbus, Ohio, US; 2008, Database Accession No. 1026450-44-1.
Extended European Search Report issued Oct. 1, 2014, in European Patent Application No. 14165664.5.

*Primary Examiner* — Venkataraman Balasubramanian
(74) *Attorney, Agent, or Firm* — Birch, Stewart, Kolasch & Birch, LLP

(57) ABSTRACT

Mercapto-containing organosilicon compounds of specific structure are low volatile and serve to enhance the adhesion of resins to inorganic substrates.

9 Claims, No Drawings

ORGANOSILICON COMPOUNDS, MAKING METHODS, AND ADHESION IMPROVER

CROSS-REFERENCE TO RELATED APPLICATION

The present application is a 37 C.F.R. §1.53(b) divisional of, and claims priority to, U.S. application Ser. No. 14/258, 105 filed Apr. 22, 2014. Application Ser. No. 14/258,105 claims priority under 35 U.S.C. §119(a) on Patent Application No. 2013-123638 filed in Japan on Jun. 12, 2013, the entire contents of which are hereby incorporated by reference.

TECHNICAL FIELD

This invention relates to novel organosilicon compounds, methods for preparing the same, and an adhesion improver comprising the same as an active ingredient.

BACKGROUND ART

Mercapto-containing organosilicon compounds are widely used as adhesion improvers for resins to inorganic substrates such as glass and metal materials. As described in JP 4692885, for example, mercapto-containing organosilicon compounds are added to epoxy resins for the purpose of improving the adhesion of the epoxy resin to a leadframe. Of the mercapto-containing organosilicon compounds, 3-mercaptopropyltrimethoxysilane and 3-mercaptopropylmethyldimethoxysilane are commonly used.

Since these mercapto-containing organosilicon compounds have low boiling points, they will volatilize off during high-temperature coating. Thus the mercapto-containing organosilicon compounds must be added more than the necessity. In addition, the surrounding equipment can be contaminated with the volatilizing compounds.

CITATION LIST

Patent Document 1: JP 4692885 (WO 2004/074344)

DISCLOSURE OF INVENTION

An object of the invention is to provide a mercapto-containing organosilicon compound which is low volatile and has high adhesion to inorganic substrates, a method for preparing the same, and an adhesion improver comprising the same.

The inventor has found that mercapto-containing organosilicon compounds having the general formulae (1) to (3) are low volatile and have high adhesion to inorganic substrates.

The invention provides organosilicon compounds, methods for preparing the same, and an adhesion improver, defined below.

[1] An organosilicon compound having the general formula (1):

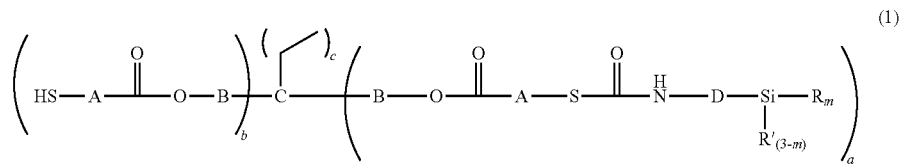

wherein A is independently a straight or branched $C_1$-$C_8$ alkylene group, B is independently a straight or branched $C_1$-$C_8$ alkylene group, D is independently a straight or branched $C_1$-$C_8$ alkylene group, R is independently a hydrolyzable group, R' is independently a $C_1$-$C_4$ alkyl group, a is a number of 1 to 4, b is a number of 0 to 3, c is 0 or 1, a+b+c is 4, and m is an integer of 1 to 3.

[2] An organosilicon compound having the general formula (2):

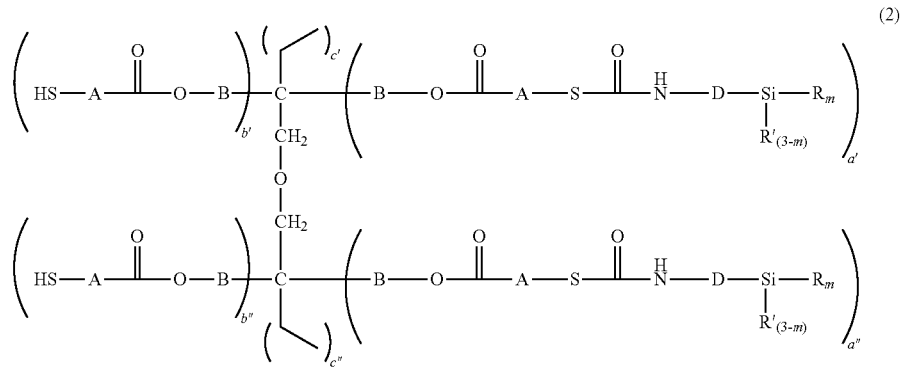

wherein A is independently a straight or branched $C_1$-$C_8$ alkylene group, B is independently a straight or branched $C_1$-$C_8$ alkylene group, D is independently a straight or branched $C_1$-$C_8$ alkylene group, R is independently a hydrolyzable group, R' is independently a $C_1$-$C_4$ alkyl group, m is an integer of 1 to 3, a' is a number of 0 to 3, b' is a number of 0 to 3, c' is 0 or 1, a'+b'+c' is 3, a" is a number of 0 to 3, b" is a number of 0 to 3, c" is 0 or 1, a"+b"+c" is 3, and a'+a" is a number of 1 to 6.

[3] An organosilicon compound having the general formula (3):

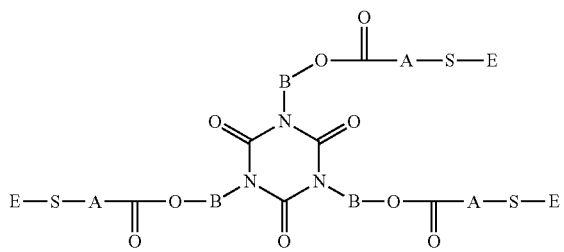

(3)

wherein A is independently a straight or branched $C_1$-$C_8$ alkylene group, B is independently a straight or branched $C_1$-$C_8$ alkylene group, E is independently hydrogen or a substituent group of the general formula (4):

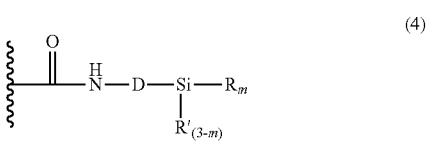

(4)

wherein D is independently a straight or branched $C_1$-$C_8$ alkylene group, R is independently a hydrolyzable group, R' is independently a $C_1$-$C_4$ alkyl group, and m is an integer of 1 to 3, at least one E being a substituent group of formula (4).

[4] The organosilicon compound of [1], having the general formula (5):

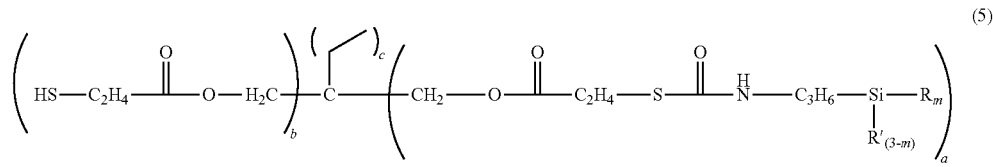

(5)

wherein R, R', m, a, b, c, and a+b+c are as defined above.

[5] The organosilicon compound of [2], having the general formula (6):

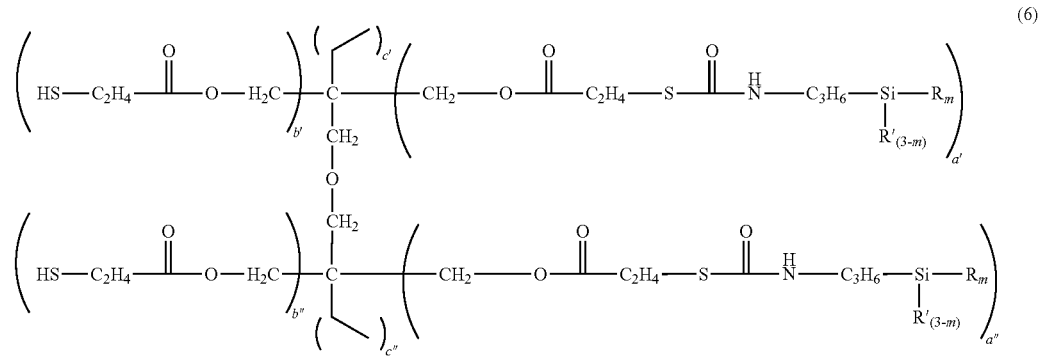

(6)

wherein R, R', m, a', b', c', a'+b'+c', a", b", c", a"+b"+c", and a'+a" are as defined above.

[6] The organosilicon compound of [3], having the general formula (7):

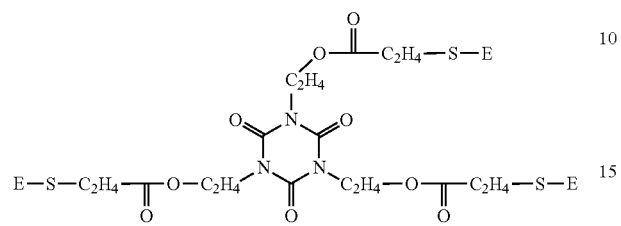

wherein E is as defined above.

[7] A method for preparing the organosilicon compound of [1], comprising the step of reacting a mercapto compound having the general formula (8):

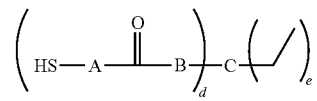

wherein A and B are as defined above, d is 3 or 4, e is 0 or 1, d+e is 4, with an isocyanate-containing organosilicon compound having the general formula (a):

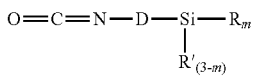

wherein D, R, R', and m are as defined above.

[8] A method for preparing the organosilicon compound of [2], comprising the step of reacting a mercapto compound having the general formula (9):

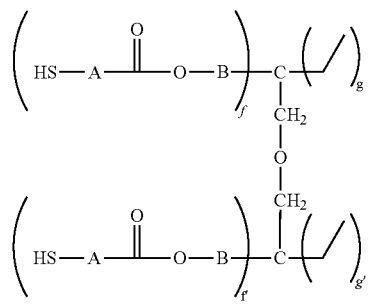

wherein A and B are as defined above, f is 3 or 4, g is 0 or 1, f+g is 4, f' is 3 or 4, g' is 0 or 1, f'+g' is 4, with an isocyanate-containing organosilicon compound having the general formula (a):

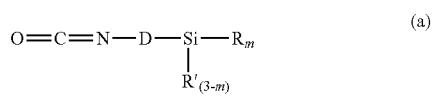

wherein D, R, R', and m are as defined above.

[9] A method for preparing the organosilicon compound of [3], comprising the step of reacting a mercapto compound having the general formula (10):

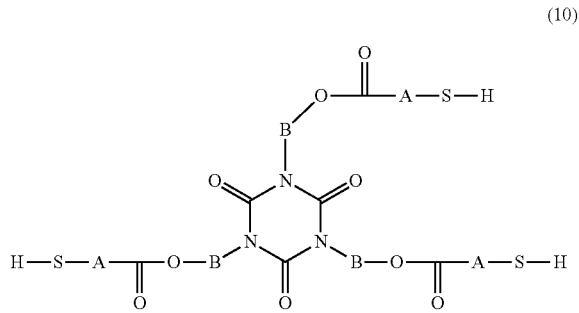

wherein A and B are as defined above, with an isocyanate-containing organosilicon compound having the general formula (a):

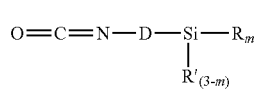

wherein D, R, R', and m are as defined above.

[10] The method of any one of [7] to [9] wherein the isocyanate-containing organosilicon compound is 3-isocyanatopropyltrimethoxysilane, 3-isocyanatopropylmethyldimethoxysilane, 3-isocyanatopropyltriethoxysilane, or 3-isocyanatopropylmethyldiethoxysilane.

[11] An adhesion improver for improving adhesion to inorganic substrates, comprising the organosilicon compound of any one of [1] to [6] as an active ingredient.

Advantageous Effects of Invention

Since the organosilicon compound of the invention has (1) a hydrolyzable silyl group, (2) a thiourethane structure, and (3) a mercapto group in a molecule, it can afford high adhesion to inorganic substrates. Since the organosilicon compound is low volatile, it causes least contamination to the surrounding equipment when used as the adhesion improver. An improvement in productivity is expectable therefrom. An economical advantage is obtained in that an improvement in adhesion is achievable with a necessary minimum amount of the compound.

DESCRIPTION OF EMBODIMENTS

Throughout the specification, Me stands for methyl. The notation "Cn-Cm" means a group containing from n to m carbon atoms per group. Herein, the "silane coupling agent" is encompassed in the "organosilicon compound."

Organosilicon Compound

One embodiment of the invention is directed to organosilicon compounds having the general formulae (1), (2), and (3).

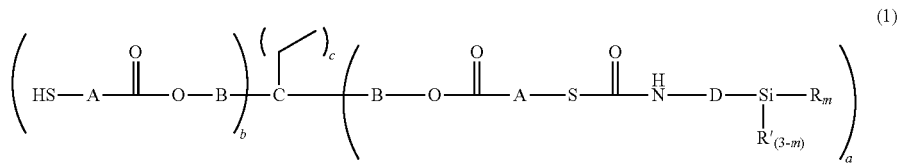

Herein A is independently a straight or branched $C_1$-$C_8$ alkylene group, B is independently a straight or branched $C_1$-$C_8$ alkylene group, D is independently a straight or branched $C_1$-$C_8$ alkylene group, R is independently a hydrolyzable group, R' is independently a $C_1$-$C_4$ alkyl group, a is a number of 1 to 4, b is a number of 0 to 3, c is 0 or 1, a+b+c is 4, and m is an integer of 1 to 3.

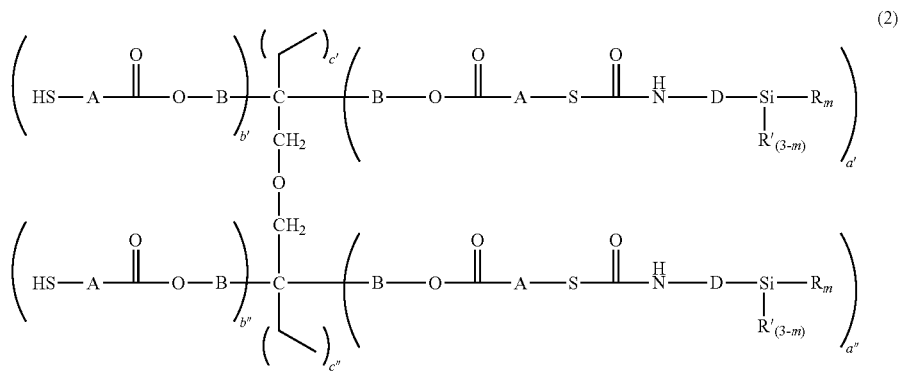

Herein A, B, D, R, R' and m are as defined above, a' is a number of 0 to 3, b' is a number of 0 to 3, c' is 0 or 1, a'+b'+c' is 3, a" is a number of 0 to 3, b" is a number of 0 to 3, c" is 0 or 1, a"+b"+c" is 3, and a'+a" is a number of 1 to 6.

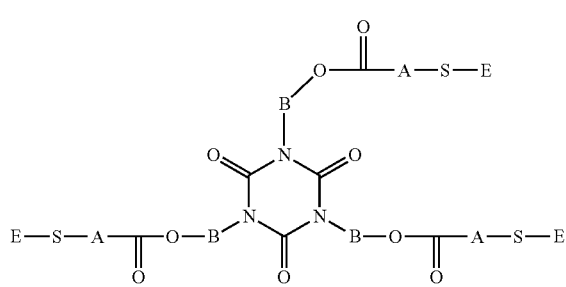

Herein A and B are as defined above, E is independently hydrogen or a substituent group of the general formula (4):

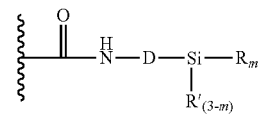

wherein D, R, R', and m are as defined above, at least one E being a substituent group of formula (4).

Specifically, suitable straight or branched $C_1$-$C_8$ alkylene groups represented by A include $CH_2$, $C_2H_4$, $C_3H_6$, $C_4H_8$, $C_5H_{10}$, $C_6H_{12}$, $C_7H_{14}$, and $C_8H_{16}$. Suitable straight or branched $C_1$-$C_8$ alkylene groups represented by B include $CH_2$, $C_2H_4$, $C_3H_6$, $C_5H_{10}$, $C_6H_{12}$, $C_7H_{14}$, and $C_8H_{16}$. Suitable straight or branched $C_1$-$C_8$ alkylene groups represented by D include $CH_2$, $C_2H_4$, $C_3H_6$, $C_4H_8$, $C_6H_{12}$, $C_2H_{14}$, and $C_8H_{16}$. It is preferred for availability of starting reactants that A be $C_2H_4$, B be $C_2H_4$, and D be $C_3H_6$. Suitable hydrolyzable groups represented by R include halogen atoms such as chlorine and bromine, and alkoxy groups such as methoxy and ethoxy. Of these, alkoxy groups are preferred, with methoxy being most preferred. Suitable $C_1$-$C_4$ alkyl groups represented by R' include methyl, ethyl, and propyl, with methyl being preferred.

The subscript m is an integer of 1 to 3, preferably 3, a is a number of 1 to 4, preferably 1 to 2, b is a number of 0 to 3, preferably 2 to 3, c is 0 or 1, and a+b+c is equal to 4. The subscript a' is a number of 0 to 3, preferably 1 to 2, b' is a number of 0 to 3, preferably 2 to 3, c' is 0 or 1, a'+b'+c' is equal to 3, a" is a number of 0 to 3, preferably 1 to 2, b" is a number of 0 to 3, preferably 2 to 3, c" is 0 or 1, a"+b"+c" is equal to 3, and a'+a" is a number of 1 to 6, preferably 1 to 3.

The preferred organosilicon compound of formula (1) has the general formula (5):

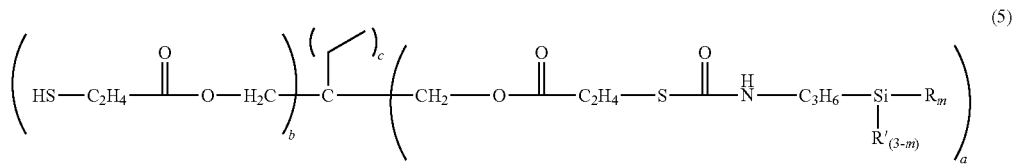

wherein R, R', m, a, b, c, and a+b+c are as defined above.

The preferred organosilicon compound of formula (2) has the general formula (6):

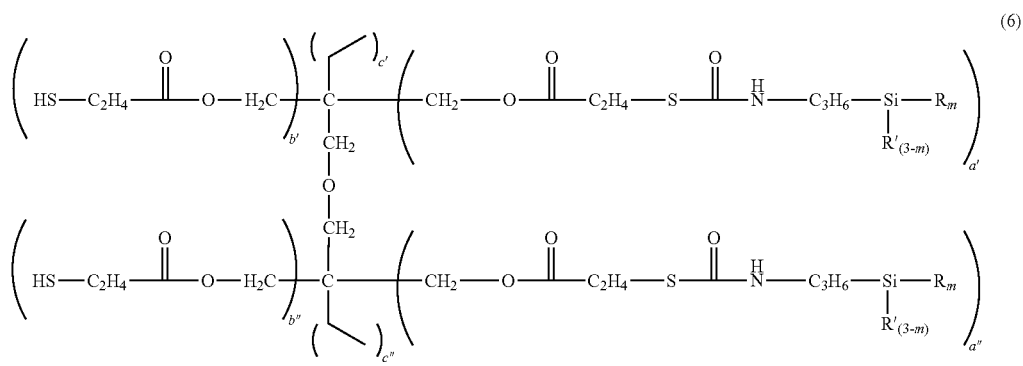

wherein R, R', m, a', b', c', a'+b'+c', a", b", c", a"+b"+c", and a'+a" are as defined above.

The preferred organosilicon compound of formula (3) has the general formula (7):

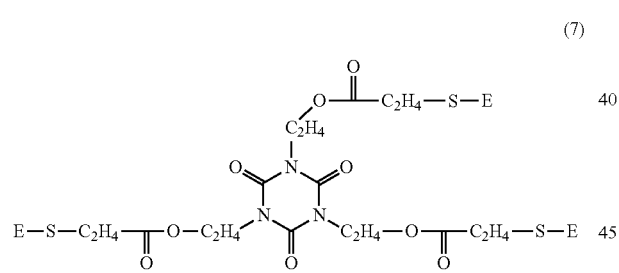

wherein E is as defined above.

Exemplary structures of the organosilicon compound of formula (1) are shown below, but not limited thereto.

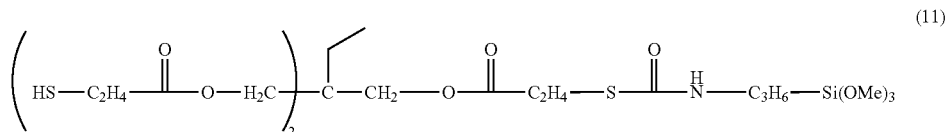

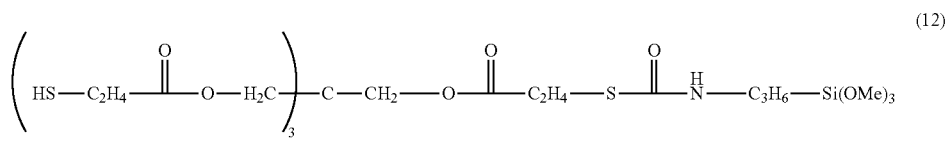

An exemplary structure of the organosilicon compound of formula (2) is shown below, but not limited thereto.

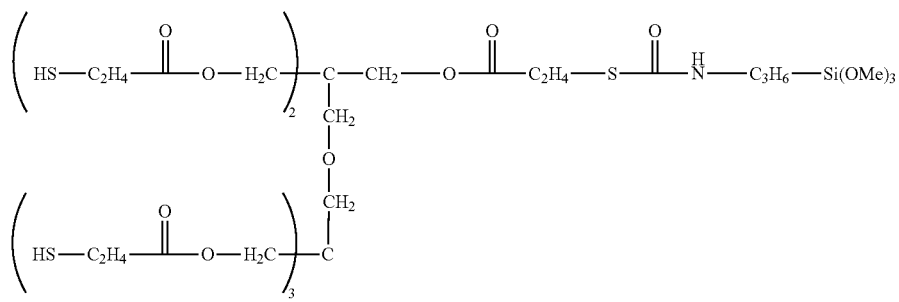

An exemplary structure of the organosilicon compound of formula (3) is shown below, but not limited thereto.

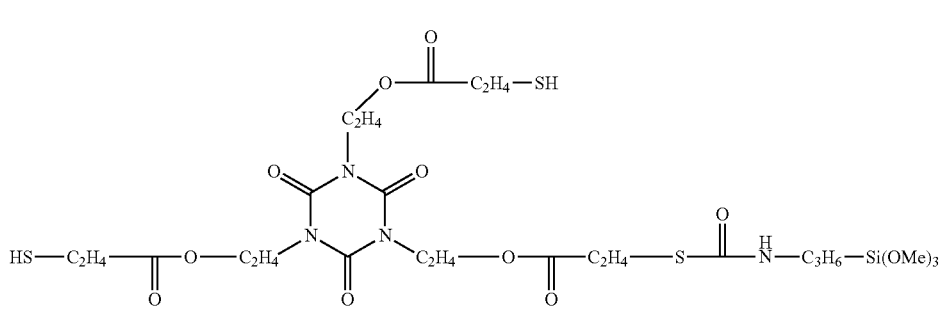

Method

Another embodiment of the invention is directed to methods for preparing the organosilicon compounds of formulae (1) to (3). The organosilicon compound of formula (1) is prepared by reacting a mercapto compound having the general formula (8):

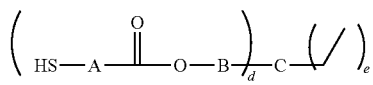

wherein A and B are as defined above, d is 3 or 4, e is 0 or 1, d+e is 4, with an isocyanate-containing organosilicon compound having the general formula (a):

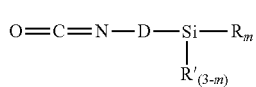

wherein D, R, R', and m are as defined above.

Examples of the mercapto compound of formula (8) include trimethylolpropane tris(3-mercaptopropionate) and pentaerythritol tetrakis(3-mercaptopropionate), but are not limited thereto.

Examples of the isocyanate-containing organosilicon compound of formula (a) include, but are not limited to, 3-isocyanatopropyltrimethoxysilane, 3-isocyanatopropylmethyldimethoxysilane, 3-isocyanatopropyltriethoxysilane, and 3-isocyanatopropylmethyldiethoxysilane.

Of these, 3-isocyanatopropyltrimethoxysilane and 3-isocyanatopropyltriethoxysilane are preferred for availability of starting reactant.

In the reaction of the mercapto compound of formula (8) with the isocyanate-containing organosilicon compound of formula (a), it is preferred to use 1 to 3 moles, especially 1 to 2 moles of the organosilicon compound per mole of the mercapto compound.

Also, the organosilicon compound of formula (2) is prepared by reacting a mercapto compound having the general formula (9):

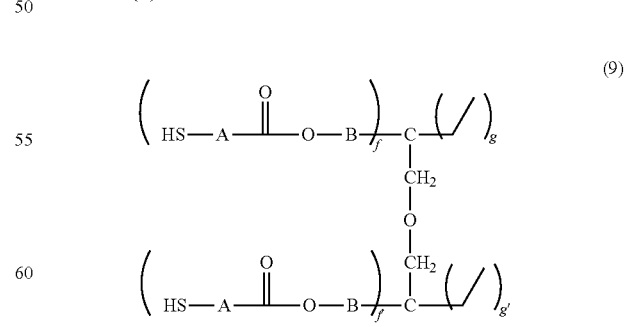

wherein A and B are as defined above, f is 3 or 4, g is 0 or 1, f+g is 4, f' is 3 or 4, g' is 0 or 1, f'+g' is 4, with an isocyanate-containing organosilicon compound having the general formula (a):

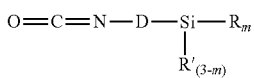

(a)

wherein D, R, R', and m are as defined above.

Exemplary of the mercapto compound of formula (9) is dipentaerythritol hexakis(3-mercaptopropionate). Examples of the isocyanate-containing organosilicon compound of formula (a) are as illustrated above, but not limited thereto.

In the reaction of the mercapto compound of formula (9) with the isocyanate-containing organosilicon compound of formula (a), it is preferred to use 1 to 6 moles, especially 1 to 2 moles of the organosilicon compound per mole of the mercapto compound.

Further, the organosilicon compound of formula (3) is prepared by reacting a mercapto compound having the general formula (10):

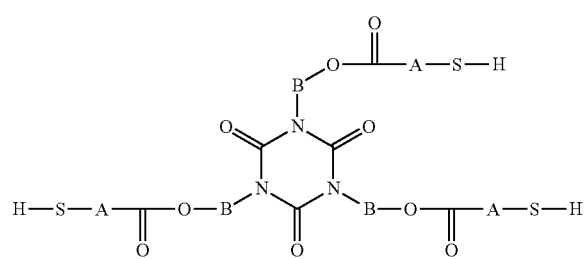

(10)

wherein A and B are as defined above, with an isocyanate-containing organosilicon compound having the general formula (a):

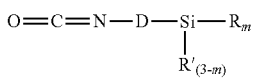

(a)

wherein D, R, R', and m are as defined above.

Exemplary of the mercapto compound of formula (10) is tris[(3-mercaptopropionyloxy)ethyl]isocyanurate. Examples of the isocyanate-containing organosilicon compound of formula (a) are as illustrated above, but not limited thereto.

In the reaction of the mercapto compound of formula (10) with the isocyanate-containing organosilicon compound of formula (a), it is preferred to use 1 to 3 moles, especially 1 to 2 moles of the organosilicon compound per mole of the mercapto compound.

As illustrated above, the organosilicon compounds of the invention may be prepared by reaction of a polyfunctional mercapto compound with an organosilicon compound having an isocyanate group. A plurality of reaction sites are involved in the reaction. In an example where a tetra-substituted mercapto compound is reacted with an organosilicon compound having an isocyanate group, there is produced a mixture of zero, mono, di, tri and tetra-substituted compounds, as shown by the general formula (15).

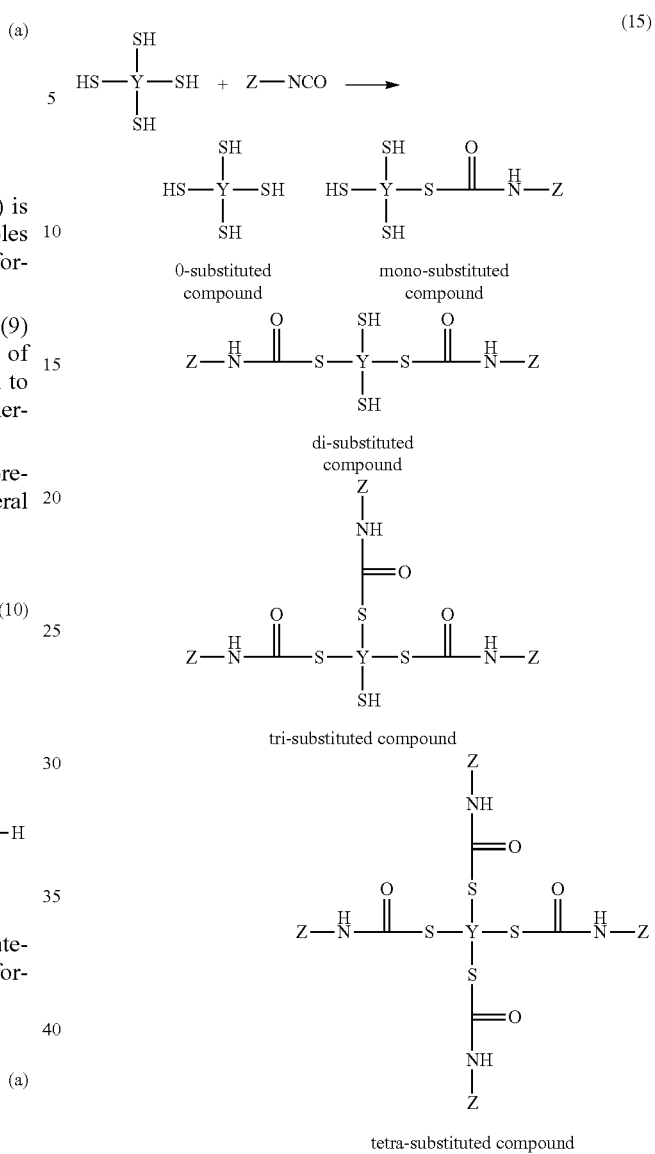

(15)

Herein, Y is a residue of the polyfunctional mercapto compound, and Z is a residue of the isocyanate-containing organosilicon compound.

Since the organosilicon compound of the invention is available as a mixture of a plurality of compounds as indicated above, the foregoing formulae (1) to (14) each represent an average composition. Therefore, even when the reaction product is a mono-substituted compound as the average composition, otherwise substituted compounds are in admixture therewith.

In preparing the organosilicon compound, a solvent may be used if necessary. The solvent used herein is not particularly limited as long as it is inert to the reactants, mercapto compound and isocyanate-containing organosilicon compound. Suitable solvents include aliphatic hydrocarbon solvents such as pentane, hexane, heptane and decane, ether solvents such as diethyl ether, tetrahydrofuran, and 1,4-dioxane, amide solvents such as formamide, dimethylformamide, and N-methylpyrrolidone, and aromatic hydrocarbon solvents such as benzene, toluene, and xylene.

In preparing the organosilicon compound, a catalyst may be used if necessary. Although the catalyst used herein may be any of the catalysts commonly used in isocyanate reaction, tin compounds and amine catalysts are preferred. As the tin catalyst, salts of tin(II) with carboxylic acids such as dioctyltin oxide are preferred for catalytic activity. Preferred amine catalysts are tertiary amines such as triethylamine, tributylamine and N-ethyldiisopropylamine. Preferably the catalyst may be used in an amount of 0.0000001 to 1 mole, more preferably 0.000001 to 0.01 mole per mole of the isocyanate-containing organosilicon compound. More than 1 mole of the catalyst may be uneconomical because the catalytic effect is saturated. Less than 0.0000001 mole of the catalyst may lead to a short catalytic effect, a low reaction rate, and low productivity.

In preparing the organosilicon compound, the reaction is exothermic. Side reactions may occur at unnecessarily high temperatures. Therefore, the reaction temperature is preferably controlled to a range of 20 to 150° C., more preferably 30 to 130° C., and even more preferably 40 to 110° C. Temperatures below 20° C. may lead to a low reaction rate and low productivity. At temperatures above 150° C., side reactions, typically polymerization reaction of the isocyanate-containing organosilicon compound may take place.

The reaction time required until the organosilicon compound is obtained is not particularly limited as long as the temperature control is possible despite exothermic reaction and exothermic reaction is completed within the time. Preferably the reaction time is 10 minutes to 24 hours, more preferably 1 to 10 hours.

The organosilicon compound of the invention finds use as an adhesion improver to inorganic substrates such as glass and metal materials. Conventional mercapto-containing organosilicon compounds are adherent to inorganic substrates such as glass and metal materials. Since the organosilicon compound of the invention has a plurality of mercapto groups per hydrolyzable group and a urethane bond and ester bond as the polar group, it is expected to exhibit higher adhesion than the conventional mercapto-containing organosilicon compounds when added to epoxy, urethane, acrylic and polyimide resins in an amount of 0.1 to 20% by weight.

EXAMPLE

Examples of the invention are given below by way of illustration and not by way of limitation. In Examples, Me stands for methyl, and IR for infrared.

Example 1

Preparation of Organosilicon Compound (11)

A 1-L separable flask equipped with a stirrer, reflux condenser, dropping funnel and thermometer was charged with 399 g (1 mol) of trimethylolpropane tris(3-mercaptopropionate) (TMMP by Sakai Chemical Industry Co., Ltd.) and 0.06 g of dioctyltin oxide and heated at 80° C. To the flask, 205 g (1 mol) of 3-isocyanatopropyltrimethoxysilane was added dropwise, followed by 2 hours of stirring at 80° C. The reaction was terminated when the complete extinction of absorption peaks assigned to the isocyanate group in the reactant was confirmed by IR spectrometry. On purification by filtration, the product was a colorless clear liquid. The mercapto equivalent was measured to be 303, which was substantially equal to the theoretical value of 301. This organosilicon compound is designated Silane A.

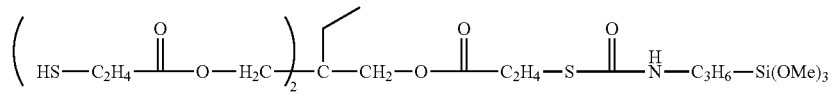

(11)

Example 2

Preparation of Organosilicon Compound (12)

A 1-L separable flask equipped with a stirrer, reflux condenser, dropping funnel and thermometer was charged with 489 g (1 mol) of pentaerythrytol tetrakis(3-mercaptopropionate) (PEMP by Sakai Chemical Industry Co., Ltd.) and 0.06 g of dioctyltin oxide and heated at 80° C. To the flask, 205 g (1 mol) of 3-isocyanatopropyltrimethoxysilane was added dropwise, followed by 2 hours of stirring at 80° C. The reaction was terminated when the complete extinction of absorption peaks assigned to the isocyanate group in the reactant was confirmed by IR spectrometry. The product was a colorless clear liquid. The mercapto equivalent was measured to be 233, which was substantially equal to the theoretical value of 231. This organosilicon compound is designated Silane B.

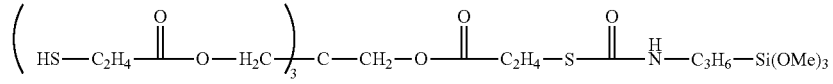

(12)

Example 3

Preparation of Organosilicon Compound (13)

A 2-L separable flask equipped with a stirrer, reflux condenser, dropping funnel and thermometer was charged with 783 g (1 mol) of dipentaerythrytol hexakis(3-mercaptopropionate) (DPMP by Sakai Chemical Industry Co., Ltd.) and 0.06 g of dioctyltin oxide and heated at 80° C. To the flask, 205 g (1 mol) of 3-isocyanatopropyltrimethoxysilane was added dropwise, followed by 2 hours of stirring at 80° C. The reaction was terminated when the complete extinction of absorption peaks assigned to the isocyanate group in the reactant was confirmed by IR spectrometry. The product was a colorless clear liquid. The mercapto equivalent was measured to be 201, which was substantially equal to the theoretical value of 197. This organosilicon compound is designated Silane C.

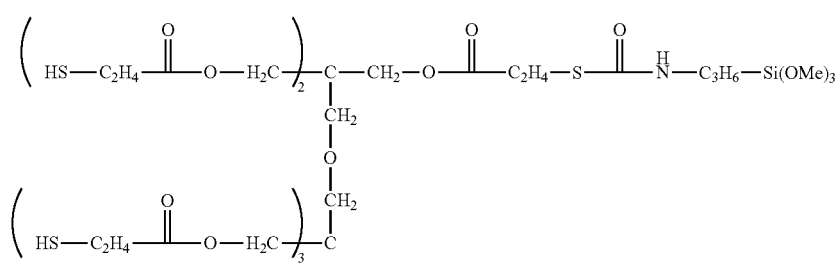

(13)

Example 4

Preparation of Organosilicon Compound (14)

A 1-L separable flask equipped with a stirrer, reflux condenser, dropping funnel and thermometer was charged with 526 g (1 mol) of tris[(3-mercaptopropionyloxy)ethyl]isocyanurate (TEMPIC by Sakai Chemical Industry Co., Ltd.) and 0.06 g of dioctyltin oxide and heated at 80° C. To the flask, 205 g (1 mol) of 3-isocyanatopropyltrimethoxysilane was added dropwise, followed by 2 hours of stirring at 80° C. The reaction was terminated when the complete extinction of absorption peaks assigned to the isocyanate group in the reactant was confirmed by IR spectrometry. The product was a colorless clear liquid. The mercapto equivalent was measured to be 370, which was substantially equal to the theoretical value of 365. This organosilicon compound is designated Silane D.

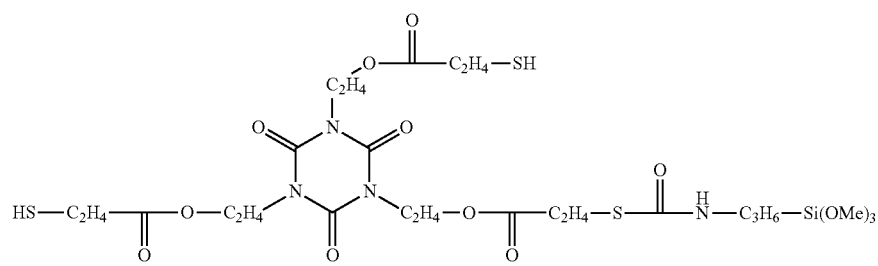

(14)

Example 5 and Comparative Example 1

Volatility of Organosilicon Compounds

The organosilicon compounds (11) to (14) obtained above, that is, Silanes A to D and Silane E (described below) were evaluated for volatility. In the test, 1 g of the compound was dropped on an aluminum dish, which was allowed to stand in an open constant-temperature chamber at 105° C. for 3 hours, after which the residue was evaluated as the nonvolatile content. A greater nonvolatile content indicates lower volatility. The results are shown in Table 1.

Silane E: 3-mercaptopropyltrimethoxysilane (KBM-803 by Shin-Etsu Chemical Co., Ltd.)

TABLE 1

|  | Compound | Nonvolatile content (%) |
|---|---|---|
| Example 5 | Silane A | 98 |
|  | Silane B | 99 |

TABLE 1-continued

|  | Compound | Nonvolatile content (%) |
|---|---|---|
|  | Silane C | 99 |
|  | Silane D | 99 |
| Comparative Example 1 | Silane E | 0 |

As seen from the data, the organosilicon compounds within the scope of the invention are least volatile. Thus the volatilization of the compound during high-temperature application is fully suppressed. The compound exerts its desired effect when added in a necessary minimum amount, with an economical advantage. In addition, contamination of the surrounding equipment is suppressed, and an improvement in productivity is expectable.

Examples 6 to 9 and Comparative Examples 2 to 4

Adhesion of Organosilicon Compounds

An epoxy resin composition to which the organosilicon compound was added was evaluated for adhesion. Specifically, the epoxy resin composition consisted of an epoxy resin YDPN638 (Nippon Steel & Sumikin Chemical Co., Ltd.), 2-methylimidazole as a catalyst, and Silane A, B, C, D or E (identified above). The composition was applied onto a glass plate to a coating thickness of 10 μm by means of a bar coater, cured at 150° C. for 1 hour, and examined by a cross-hatch adhesion test according to JIS K-5400. The formulation (in parts by weight) of the composition is shown in Table 2 together with the test results.

TABLE 2

| Formulation | Example | | | | Comparative Example | | |
|---|---|---|---|---|---|---|---|
| (pbw) | 6 | 7 | 8 | 9 | 2 | 3 | 4 |
| Epoxy resin | 98 | 98 | 98 | 98 | 98 | 98 | 98 |
| Catalyst | 2 | 2 | 2 | 2 | 2 | 2 | 2 |

TABLE 2-continued

| Formulation | Example | | | | Comparative Example | | |
|---|---|---|---|---|---|---|---|
| (pbw) | 6 | 7 | 8 | 9 | 2 | 3 | 4 |
| Silane A | 0.5 | | | | | | |
| Silane B | | 0.5 | | | | | |
| Silane C | | | 0.5 | | | | |
| Silane D | | | | 0.5 | | | |
| Silane E | | | | | 2.0 | 0.5 | |
| Test results | | | | | | | |
| Adhesion | 100/100 | 100/100 | 100/100 | 100/100 | 90/100 | 70/100 | 50/100 |

As seen from the test results, the organosilicon compounds within the scope of the invention are effective for improving the adhesion of epoxy resin compositions to glass substrates even in a minimal amount of addition.

Japanese Patent Application No. 2013-123638 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organosilicon compound having the formula (2):

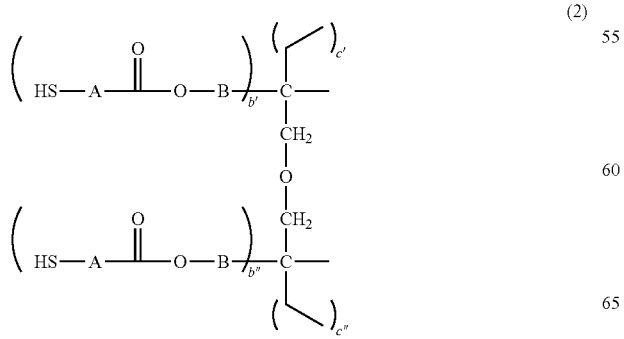

(2)

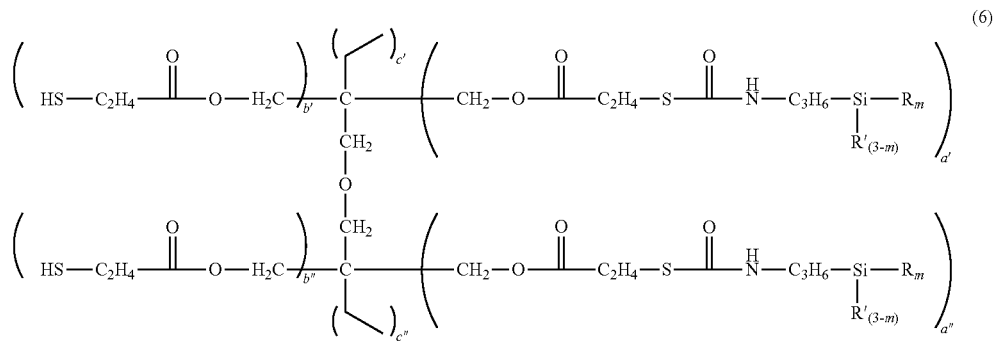

wherein A is independently a straight or branched $C_1$-$C_8$ alkylene group, B is independently a straight or branched $C_1$-$C_8$ alkylene group, D is independently a straight or branched $C_1$-$C_8$ alkylene group, R is independently a hydrolyzable group, selected from the group consisting of halogen atoms and alkoxy groups, R' is independently a $C_1$-$C_4$ alkyl group, m is an integer of 1 to 3, a' is a number of 0 to 3, b' is a number of 0 to 3, c' is 0 or 1, a'+b'+c' is 3, a" is a number of 0 to 3, b" is a number of 0 to 3, c" is 0 or 1, a"+b"+c" is 3, and a'+a" is a number of 1 to 6.

2. The organosilicon compound of claim 1, having the formula (6):

(6)

wherein R, R', m, a', b', c', a'+b'+c', a", b", c", a"+b"+c", and a'+a" are as defined in claim 1.

3. A method for preparing the organosilicon compound of claim 1, comprising the step of reacting a mercapto compound having the formula (9):

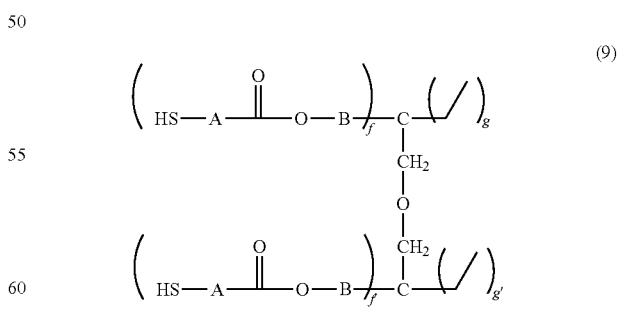

(9)

wherein A and B are as defined in claim 1, f is 3 or 4, g is 0 or 1, f+g is 4, f' is 3 or 4, g' is 0 or 1, f'+g' is 4, with an isocyanate-containing organosilicon compound having the formula (a):

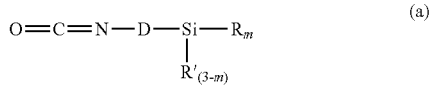

(a)

wherein D, R, R', and m are as defined in claim 1.

4. The method of claim 3 wherein the isocyanate-containing organosilicon compound is 3-isocyanatopropyltrimethoxysilane, 3-isocyanatopropylmethyldimethoxysilane, 3-isocyanatopropyltriethoxysilane, or 3-isocyanatopropylmethyldiethoxysilane.

5. A resin composition having improved adhesion to inorganic substrates, said composition comprising;
 0.1 to 20 weight-% of the organosilicon compound of claim 1 as an active ingredient; and
 a resin selected from the group consisting of epoxy resins, urethane resins, acrylic resins, and polyimide resins.

6. A resin composition having improved adhesion to inorganic substrates, said composition comprising;
 0.1 to 20 weight-% of the organosilicon compound of claim 2 as an active ingredient; and
 a resin selected from the group consisting of epoxy resins, urethane resins, acrylic resins, and polyimide resins.

7. The organosilicon compound of claim 1, wherein each R is independently selected from the group consisting of chlorine, bromine, ethoxy, and methoxy.

8. The organosilicon compound of claim 1, wherein
 each A is independently selected from the group consisting of $CH_2$, $C_2H_4$, $C_3H_6$, $C_4H_8$, $C_5H_{10}$, $C_6H_{12}$, $C_7H_{14}$, and $C_8H_{16}$,
 each B is independently selected from the group consisting of $CH_2$, $C_2H_4$, $C_3H_6$, $C_4H_8$, $C_5H_{10}$, $C_6H_{12}$, $C_7H_{14}$, and $C_8H_{16}$,
 each D is independently selected from the group consisting of $CH_2$, $C_2H_4$, $C_3H_6$, $C_4H_8$, $C_5H_{10}$, $C_6H_{12}$, $C_7H_{14}$, and $C_8H_{16}$, and
 each R' is independently selected from the groups consisting of methyl, ethyl, and propyl.

9. The organosilicon compound of claim 1, wherein:
 the subscript m is an integer of 1 to 3, the subscript a is a number of 1 to 4, the subscript b is a number of 0 to 3, the subscript c is 0 or 1, and a+b+c is equal to 4;
 the subscript a' is a number of 0 to 3, the subscript b' is a number of 0 to 3, the subscript c' is 0 or 1, and a'+b'+c' is equal to 3,
 the subscript a" is a number of 0 to 3, the subscript b" is a number of 0 to 3, the subscript c" is 0 or 1, and a"+b"+c" is equal to 3, and
 a'+a" is a number of 1 to 6.

\* \* \* \* \*